United States Patent [19]
Adair

[11] 4,431,420
[45] Feb. 14, 1984

[54] GLASS-CERAMIC DENTAL PRODUCTS

[75] Inventor: Peter J. Adair, Brookline, Mass.

[73] Assignee: Corning Glass Works, Corning, N.Y.

[21] Appl. No.: 373,617

[22] Filed: Apr. 30, 1982

Related U.S. Application Data

[63] Continuation-in-part of Ser. No. 227,810, Jan. 27, 1981, abandoned, which is a continuation of Ser. No. 57,399, Jul. 13, 1979, abandoned.

[51] Int. Cl.$^3$ ............................................... A61K 6/08
[52] U.S. Cl. ..................................... 433/199; 106/35; 433/201; 433/202; 433/212; 433/222; 501/3
[58] Field of Search ............... 433/199, 201, 202, 212, 433/177, 218, 222; 106/35; 501/3

[56] References Cited

U.S. PATENT DOCUMENTS 3,689,293  9/1972  Beall ................................. 106/39.6
3,732,087  5/1973  Grossman .......................... 65/30

Primary Examiner—Lorenzo B. Hayes
Attorney, Agent, or Firm—C. S. Janes, Jr.

[57] ABSTRACT

Precision dental tools, models, appliances, prostheses, and attachments are produced by providing a glass body of selected conformation, and then heat treating the glass body to yield a glass-ceramic component of superior characteristics wherein tetrasilicic fluormica constitutes the predominant crystal phase.

1 Claim, 4 Drawing Figures

GLASS-CERAMIC DENTAL PRODUCTS

This application is a continuation-in-part of application Ser. No. 227,810, filed Jan. 27, 1981, now abandoned, which was a continuation of application Ser. No. 57,399, filed July 13, 1979, now abandoned.

BACKGROUND OF THE INVENTION

1. Field of the Invention

The present invention relates to dental products and processes and, more particularly, to the fabrication of precision dental models, dental tools, dental appliances, dental attachments, and dental prosthetic devices.

2. Prior Art

A major purpose of the dental profession is to replace or correct damaged or deformed tooth structure or condition by fabricating and installing dental constructs such as dental appliances, e.g., artificial denture plates, bridges, and orthodontic brackets, attachments therefore, and prosthetic devices, e.g., inlays, onlays, partial or full dentures, and crowns. All such products ideally (1) should be inert in the oral environment, (2) should resist the forces of mastication, (3) should be capable of assuming physiologically compatible anatomical configuration, and (4) should exhibit aesthetic qualities similar to those of natural teeth. Dental tools are not required to meet the last three criteria but must exhibit good strength as well as inertness to oral environments.

Present dental constructs are customarily composed of metal alloys, porcelain, amalgam, or acrylic polymers and combinations thereof, which do not completely meet the foregoing ideal requirements. Metal alloys and amalgam are undesirable in locations where aesthetics is a major consideration because they sharply differ from teeth in optical characteristics. Porcelain and acrylic polymers are either too brittle or too weak to resist masticatory forces in many locations. Composite structures, as in the case of an alloy substructure for strength and a porcelain superstructure for appearance, are extremely technique sensitive and are too bulky in many situations. In other words, prior dental constructs have been at best a compromise among the four ideal requirements.

SUMMARY OF THE INVENTION

The present invention is based upon the discovery that dental constructs exhibiting visual appearances similar to those of tooth enamel, having expansion coefficients and thermal conductivities approximating those of tooth enamel, and demonstrating mechanical strengths at least as great as those of composite tooth structures can be readily fabricated from glass-ceramic materials. Such materials are also useful in the fabrication of dental tools.

Glass-ceramics had their genesis in U.S. Pat. No. 2,920,971 and their production comprehends three fundamental steps. First, a glass-forming batch of a predetermined composition is melted. Second, that melt is simultaneously cooled to a temperature at least below the transformation range thereof and shaped into a glass body of a desired configuration. Third, that glass shape is subjected to a particular heat treatment to cause the in situ development and growth of crystals therewithin such that the glass is converted into a predominantly and, frequently, essentially totally crystalline article.

The transformation range is defined as that temperature at which a liquid melt is deemed to have been transformed into an amorphous solid, that temperature typically being considered as lying in the vicinity of the annealing point of a glass. If desired, the glass melt can be cooled all the way to room temperature to permit visual inspection thereof for glass quality. However, in the interests of production speed and energy economy, the commercial manufacture of glass-ceramics commonly involves cooling the initial melt to only slightly below the transformation range and then proceeding with the crystallization heat treatment. The crystallization heat treatment commonly follows a two-step practice; viz., the glass body is first heated to a temperature in or somewhat above the transformation range and maintained thereat for a sufficient length of time to cause the development of nuclei and to initiate crystallization, and, thereafter, the nucleated body is heated to a higher temperature, which may approach or, most often, will exceed the softening point of the glass, and held at the temperature for a sufficient length of time to effect the growth of crystals on the nuclei. These two steps have been termed nucleation and crystallization, respectively.

Because a glass-ceramic is derived through the controlled crystallization of a glass, all the many forming methods known to the glass technologist can be utilized in achieving a desired product shape. But, because of the highly crystalline microstructure inherent in glass-ceramics, the physical properties exhibited thereby will be more closely akin to those of the crystal phases present therein than to those of the parent glass body. As a corollary to that factor, the physical properties demonstrated by whatever residual glass is included in a glass-ceramic body will be quite distinct from those of the precursor glass, since the components of the crystal phase will have been removed therefrom. Finally, inasmuch as the glass-ceramic body results from the in situ crystallization of a glass, it will exhibit the same geometry as the parent glass body and be free from voids and non-porous.

Reference is hereby made to that patent for further information relating to the production, microstructure, and physical properties of glass-ceramic articles.

In the broadcast terms, the method of the instant invention contemplates four basic elements. First, a glass-forming batch of a desired composition is melted. Second, the melt is cast into a mold or otherwise shaped, as by compression molding, centrifugal casting, or injection molding, to form a glass body having an intermediate configuration with at least one selected surface of particular conformation. Third, the glass body will be heat treated in a particular manner to crystallize it in situ and thereby convert it into a glass-ceramic body of corresponding intermediate shape. Fourth, selected surfaces of the glass-ceramic body will be machined or otherwise formed into a dental tool or construct of final shape.

The glass-ceramic compositions operable as dental constructs are limited only by the constraints that they: (a) be inert in the oral environment; (b) be sufficiently strong to resist the forces of mastication, i.e., exhibit a tensile strength as defined in terms of modulus of rupture greater than 8000 psi; (c) be capable of assuming physiologically compatible anatomical configuration; (d) have coefficients of thermal expansion and thermal conductivities approximating those of tooth structure; and (e) will preferably exhibit a visual appearance similar to that of tooth structure. This latter is not absolutely mandatory since an outer layer, e.g., porcelain, can be applied thereto. However, such practice adds expense and involves careful matching of the properties of the porcelain and substrate material. The material for dental tools must be inert in the oral environment, possess a modulus of rupture greater than 8000 psi, and be capable of ready shaping.

As was noted above, U.S. Pat. No. 2,920,971 provides the basic disclosure in the field of glass-ceramics and numerous exemplary compositions are set forth therein. However, as has been alluded to above, the final configuration of dental constructs and dental tools is customarily achieved through machining of the body material. This capability of being machined or otherwise mechanically shaped with relative ease, utilizing conventional steel tools, is particularly demonstrated in glass-ceramics wherein a mica constitutes the predominant crystal phase. Numerous glass-ceramics containing synthetic fluormica crystals have been disclosed in the prior art.

Mica-containing glass-ceramics demonstrate a relatively unique property which renders them particularly desirable in applications such as dental tools and constructs. Thus, such bodies manifest deviations from brittle behavior which permit them to withstand point impact with limited fracture propagation. For example, those bodies can be indented in a point hardness test procedure where conventional porcelains are fractured. This capability of mica-containing glass-ceramics is due to the fact that the crystal phase can flow plastically to some extent through translational gliding along the basal or cleavage plane.

U.S. Pat. No. 3,689,293 is explicitly directed to glass-ceramic bodies demonstrating excellent machinability accompanied with good mechanical strength and impact resistance. Those glass-ceramics contain fluorophlogopite solid solution as the predominant crystal phase and have an overall composition consisting essentially, by weight on the oxide basis, of about 25–60% $SiO_2$, 15–35% $R_2O_3$, wherein $R_2O_3$ consists of 3–15% $B_2O_3$ and 5–25% $Al_2O_3$, 2–20% $R_2O$, wherein $R_2O$ consists of 0–15% $Na_2O$, 0–15% $K_2O$, 0–15% $Rb_2O$, and 0–20% $Cs_2O$, 6–25% $MgO+Li_2O$ consisting of 4–25% MgO and 0–7% $Li_2O$, and 4–20% F. The precursor glass bodies are converted to glass-ceramics via heat treatment at temperatures between about 750°–1100° C. The preferred heat treatment consists of nucleating at about 750°–850° C. followed by crystallization at about 850°–1100° C. Such products can be very readily shaped into dental constructs and dental tools.

However, whereas not as readily machinable as the materials prepared from U.S. Pat. No. 3,689,293, the most preferred compositions for use as dental constructs and dental tools are those disclosed in U.S. Pat. No. 3,732,087. These latter compositions not only demonstrate somewhat superior chemical durability and mechanical strength, e.g., modulus of rupture values up to 30,000 psi, but also exhibit two other very important features—one cosmetic and the other of practical significance. First, the crystallized products closely approximate the translucency-opacity characteristics of natural teeth. Second, the materials display wearing properties quite similar to those of natural teeth, i.e., the hardness and abrasion resistance are very comparable such that the glass-ceramic product wears at about the same rate as natural teeth. This latter faculty makes for long term comfort and efficient mastication.

The glass-ceramic materials of U.S. Pat. No. 3,732,087 demonstrate good machinability and contain tetrasilicic mica as the predominant crystal phase. The base compositions therefor consist essentially, by weight on the oxide basis as calculated from the batch, of about 45–70% $SiO_2$, 8–20% MgO, 8–15% $MgF_2$, 5–35% $R_2O+RO$, wherein $R_2O$ ranges from about 5–25% and consists of at least one oxide selected in the indicated proportion from the group of 0–20% $K_2O$, 0–23% $Rb_2O$, and 0–25% $Cs_2O$, and wherein RO ranges from about 0–20% and consists of at least one oxide selected from the group of SrO, BaO, and CdO. As optional ingredients, up to 10% $Sb_2O_5$ and/or up to 5% of conventional glass colorants may be present. The parent glass bodies are crystallized in situ to glass-ceramics by nucleating at 650°–850° C. followed by crystallization at about 800°–1200° C. As observed therein, a period of about 0.25–10 hours is generally sufficient to induce nucleation and about 1–100 hours will customarily be utilized in the crystallization step to insure a high proportion of crystals in the product. Finally, compositions consisting essentially of about 55–65% $SiO_2$, 12–20% MgO, 9–13% $MgF_2$, 7–18% $K_2O$, and 0.5–8% $As_2O_5$ are preferred for their machinability character.

Nevertheless, whereas machinability is a vital characteristic necessary for utility in the production of dental constructs and tools, three other factors must also be evaluated regarding the suitability of glass-ceramic compositions for dental application; viz, visual appearance, chemical durability, and the capability of being processed via traditional dental laboratory techniques. The first two were alluded to briefly above.

In working with the inventive materials, the quality of visual appearance has been assessed in terms of translucency, since the property can be quantified and is the key optical attribute for a dental material. Other characteristics such as color and vitality are also important, of course, but, if the translucency of a material does not fall within a given range, the body will not function aesthetically.

Chemical durability is of critical significance since a dental construct must endure a warm and wet environment over a pH regime normally varying between about 6–8, with occasional excursions outside that range. An accelerated procedure for determining the long term durability of the inventive materials was developed.

Two vital factors require consideration when judging a material candidate for processing in a dental laboratory. The most important characteristic is the sag evidenced by the material, that is, the capability to maintain body geometry during a heat treatment cycle. Although dental constructs are prepared in an investment which helps in holding shape and dimensions, a minimum degree of stiffness is required. The second significant process variable is the amount of contraction experienced by the material resulting from densification as the precursor glass is converted to a glass-ceramic. This value is customarily expressed as percent linear contraction and is calculated from density data.

Based upon those criteria, compositions operable to provide the most ideal combination of translucency, chemical durability, and processibility, as well as high strength and machinability, consist essentially, expressed in terms of weight percent on the oxide basis, of

| | |
|---|---|
| $K_2O$ | 10–18 |

| | -continued |
|---|---|
| MgO | 14–19 |
| SiO$_2$ | 55–65 |
| Al$_2$O$_3$ | 0–2 |
| ZrO$_2$ | 0–7 |
| F | 4–9 | wherein BaO and/or SrO may optionally be substituted for up to 50% of the K$_2$O on the molar basis.

To insure the highest chemical durability and resistance to staining from foods, the preferred compositions will contain 1–9% Al$_2$O$_3$+ZrO$_2$ with the most preferred materials containing at least 0.5% Al$_2$O$_3$ and/or at least 2% ZrO$_2$. Conventional glass colorants may optionally be included in customary amounts and, although significantly increasing the cost of the inventive materials, a substantial proportion of the K$_2$O content may optionally be replaced on the molar basis with Rb$_2$O and/or Cs$_2$O. The inventive glasses are generally sufficiently fluid that no fining agent is necessary. If such an agent should be required, however, As$_2$O$_3$ and/or Sb$_2$O$_3$ will not be utilized to forestall any possible toxic effects.

The use of glass-ceramic materials for fabricating dental crowns and inlays was suggested by W. T. MacCulloch in "Advances in Dental Ceramics," *British Dental Journal*, Apr. 16, 1968, pages 361–5. The author noted the use of a metal phosphate as a nucleating agent and formed a tooth from a glass-ceramic composition within the Li$_2$O-ZnO-SiO$_2$ system. MacCulloch also observed that, through the use of silver as the nucleating agent, the parent glass became photosensitive such that, through differential exposure of the glass with ultraviolet radiation, differences in crystallization can be achieved, thereby simulating the polychromatic effect of natural teeth. The only composition data provided comprised the single reference to Li$_2$O-ZnO-SiO$_2$ glass-ceramics with no details as to amounts of each component.

U.S. Pat. No. 4,189,325 describes the use of glass-ceramic materials in dental restorations. The compositions therefor consist essentially, expressed in terms of mole percent on the oxide basis, of about 25–33% Li$_2$O, 1–10% CaO, 0.5–0.5% Al$_2$O$_3$, and 52–73.5% SiO$_2$ to which are added 0.003–0.01% by weight platinum and 0.2–2% by weight Nb$_2$O$_5$ as nucleating agents. No data regarding the identity of the crystallization developed are provided, but the compositions thereof self-evidently preclude the formation of fluormica crystals which give rise to the machinability characteristics exhibited by the glass-ceramics forming the basis of the present invention.

Brief Description of the Drawings

For a fuller understanding of the nature and objects of the present invention, reference is made to the following detailed description, which is to be taken in connection with the accompanying drawings, wherein.

DETAILED DESCRIPTION OF THE PREFERRED EMBODIMENT

Figure 1:
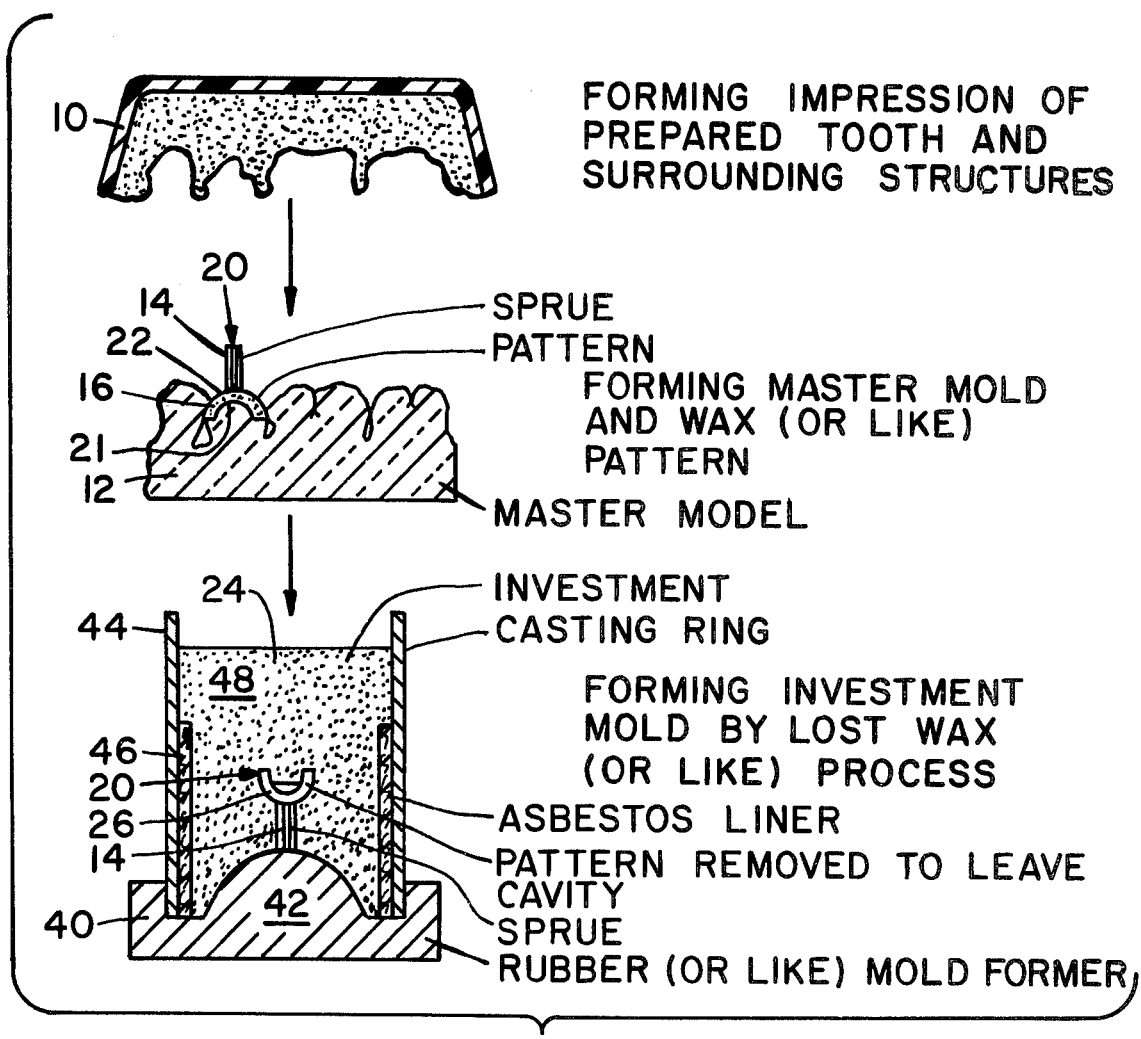
FIG. 1 illustrates producing an investment mold in accordance with the present invention.

Generally, with reference to the drawings, the process of the present invention comprises the following steps. First, an impression 10 is formed conventionally by pressing a soft dental impression composition (e.g., silicon rubber, wax, mercaptan rubber, and the like) against prepared dental surfaces of specified configuration and solidifying the resulting shape. Next, this is filled with dental stone (e.g. plaster of Paris) to form a master model 12. Next, a wax (or the like) pattern 20 of the dental construct, characterized by a sprue 14 and a pattern body 16, is prepared in association with the master model. In this case, the prepared dental surfaces are presented by the prepared facets of a tooth to be restored and the specified configuration is shown as involving the reentrant, but not undercut, inward facets 21 of a restoration having an anatomical outward surface 22. Next, wax pattern 20 is imbedded in a refractory investment slurry 24, which is permitted to solidify. Next, the investment is heated to remove the wax from the resulting mold cavity 26. The investment slurry material typically is a phosphate-bonded or silicate-bonded inert cementitious clay or other silicate. A batch of a predetermined composition or a preferred glass shape is heated to a temperature of from about 1325° to 1500° C. in a refractory crucible, composed for example of platinum, alumina, silica, mullite, or zirconia. The resultant melt is injected into the mold, which normally will have been heated to a temperature of from 700° to 950° C. to forestall cracking or breakage thereof from thermal shock, under a back air pressure of, for example, from about 8 to 50 psig. A vacuum may be applied in conjunction with the back air pressure to assist in insuring complete filling or, if desired, sufficient vacuum may be applied alone to suck the melt into the mold. In general, the vacuum will range between about 0.2 to 1.0 bar. Also, as can be appreciated, mechanical means, such as a piston, injection molding, or centrifugal casting can be utilized to fill the mold cavity. Centrifugal forces ranging about 1–15 psig have been found very satisfactory for this purpose.

Under these circumstances, the contraction rate of the mold cavity during cooling will closely match the contraction rate of the melt so that little or no compression is exerted by the mold on the casting. Initially, the elevated temperature of the melt does not affect the temperature of the mold because the mass of the melt is relatively small. Next, the mold and its contents are allowed to cool to room temperature and a clear parent glass casting 28, certain of its surfaces 30 being of the original specified configuration, is removed from the mold. The transparency permits the casting to be readily inspected visually for any flaws. As shown, the parent glass casting 28 generally is in the shape of a cap having, in addition to dome-shaped surface 32, a residual sprue 34 and button 35, which have resulted from the aforementioned casting steps. Then parent glass casting 28, conveniently touching only sprue 34, is heat treated at a temperature and for a time sufficient to cause in situ crystallization thereof such that the casting is converted from a glass to a predominantly crystalline body. Then, certain surfaces of this dental component are machined, employing conventional dental drills and mills to produce the finely desired shape. As shown, glass-ceramic component 36 is ground at 38 to sever sprue 34 and to provide a polished, anatomically-shaped surface. Thereafter, the outer surface of the component is optionally polished to provide a smooth and glossy appearance. Also, if desired, the dental component is optionally colored and/or glazed to conform the appearance of the component to that of tooth structure with which it is to be associated.

In the tetrasilicic fluorine micas which crystallize from the starting glasses to form the preferred glass-ceramic materials, the X, Y and Z positions are believed to be filled in the following manner: X position K; Y position Mg; and Z position Si. These micas, which normally have the postulated formula $KMg_{2.5}Si_4O_{10}F_2$, are described as tetrasilicic because they do not display Al- or B-for-Si substitutions in the $Z_2O_5$ hexagonal sheets of the mica layer as do the fluorophlogopites ($KMg_3AlSi_3O_{10}F_2$) or ($KMg_3BSi_3O_{10}F_2$), such as comprise the predominant crystal phases in the products of U.S. Pat. No. 3,689,293. Those crystals have been termed trisilicic fluormicas.

In general, the dental laboratory will not melt the batch materials to produce the precursor glass since very high temperatures and stirring are utilized to insure a homogeneous body. Rather, the dental laboratory will commonly purchase the precursor glass from a glass manufacturer in some convenient form, e.g., buttons, marbles, or other small shapes. This glass preform can then be remelted in the laboratory and will be poured into a mold at a temperature above its liquidus or otherwise shaped to form a glass body having at least one surface of a particular conformation. Heat treatment is effected after the melt has been cooled below its transformation range and is continued until nuclei are first formed throughout the glass followed by the growth of fluormica crystals on those nuclei.

The resulting glass-ceramic compositions are such that they are typically characterized by a white or off-white color, unless colorants have been deliberately added to the batch. The intermediate glass component has a characteristic clear or somewhat hazy vitreous structure. The final glass-ceramic product consists essentially of tetrasilicic fluormica crystals homogeneously dispersed within a residual glassy matrix, the crystals constituting the predominant proportion of the body. In general, the higher the proportion of crystals, the more desirable the product.

Figure 2:
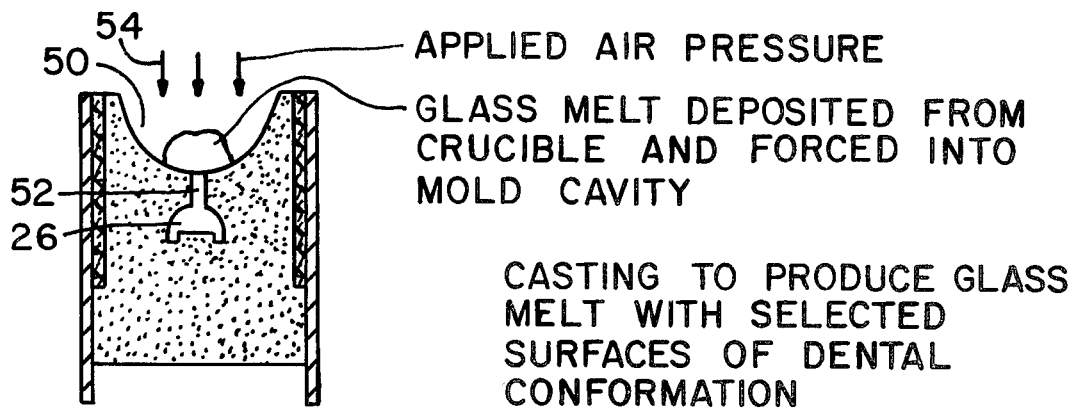
FIG. 2 illustrates forming a parent glass casting in accordance with the present invention.
Figure 3:
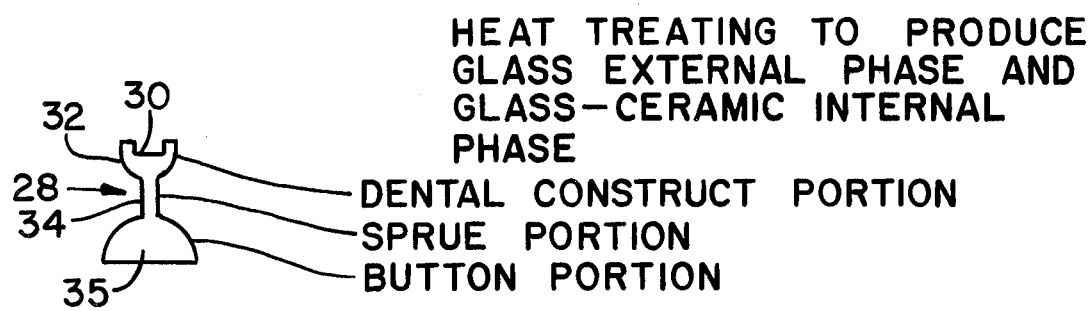
FIG. 3 illustrates heat treating the casting to form a glass-ceramic component in accordance with the present invention.
Figure 4:
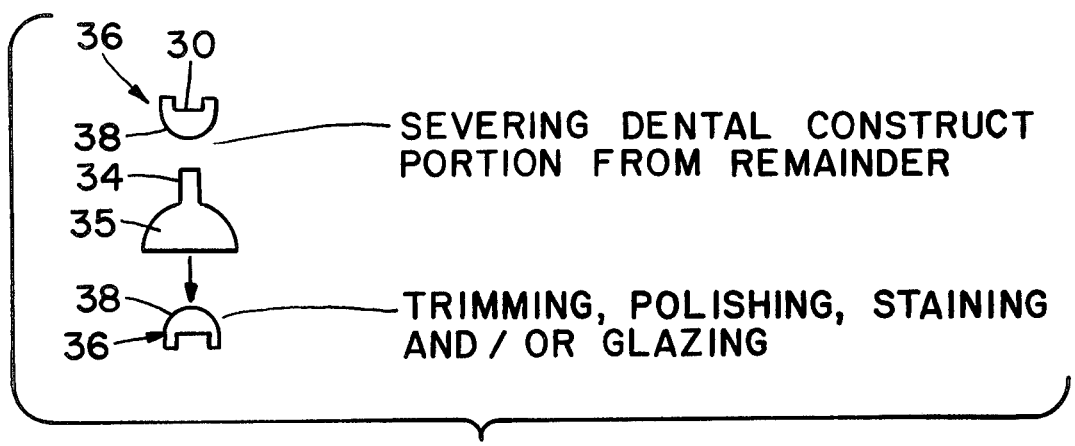
FIG. 4 illustrates machining the glass-ceramic component to provide a final dental construct.

The foregoing process contemplates the production of a variety of dental tools and constructs of the foregoing compositions. The dental constructs considered here are deemed to fall under the four general categories of dental models, dental appliances, dental attachments, and prosthetic devices. Typically, the inlays are of the type that have inward walls or facets of a tooth and outward walls or facets that are in continuity with the external contour of the tooth. Customarily, as described above with reference to FIGS. 1 to 4, the caps or crowns are of the type that fit over and cover the prepared crown form or root canal post of a tooth stump, having lower inward walls or facets that conform to prepared outer walls or facets of the tooth stump and upper outward walls or facets that are in continuity with the external contour of the tooth. Commonly, the prostheses are of the type that replace dental and/or related structures in the oral cavity, for example, false teeth, dentures and components thereof.

Example

With reference to the drawings, the illustrated process of the present invention comprises the following steps for producing a dental restoration. A wax pattern is formed conventionally and, as shown at 20, is mounted on the upper end of sprue 14. The lower end of the sprue is attached to a cylindrical casting form 40 by a soft wax bond 42. Wax bond 42 is manipulated to provide continuously smooth joints. Wax pattern 20 is painted with polar surfactant solution, e.g., either aqueous or alcohol, to minimize tackiness and is blown dry with an air stream. Wax pattern 20 is surrounded by a metal casting ring 44, which has an asbestos or other thermal insulating liner 46. An investment slurry 48 is prepared by mixing a refractory such as silica flour and an aqueous liquid such as water-ethyl silicate solution. The investment slurry is first painted onto the wax pattern and then is poured into the casting ring so as to cover the pattern completely, but to a height of no more than about one-half inch (1.25 centimeters) above the wax pattern. The investment slurry is allowed to set for approximately forty-five minutes to form a green investment mold. To cure this green investment mold, it is placed into a cold furnace, heated to approximately 650° C. (1200° F.) in a one hour period of gradually increasing temperature, and is maintained within the temperature range of approximately 650°–950° C. for a one hour period of steady temperature.

The cured investment mold is thereafter removed from the casting form and casting ring and inverted to provide precision cavity 26 which communicates with a dished upper mouth 50 through a port 52, the wax and the plastic tube having been burned out during the curing period. Into this cavity through a suitable port is poured the melt of, for example, a tetrasilicic fluormica composition, which has been heated in a suitable crucible to a temperature providing adequate fluidity. The melt is forced through depression 50 and port 52 into cavity 26 by a backup air pressure 54 of approximately 8 pounds per square inch (0.56 kg/cm$^2$, which is maintained until the melt has solidified to a glass.

After the casting is cooled to room temperature, the bulk of the investment material is removed mechanically from the glass casting and residual adhering fragments are removed by application of an investment solvent liquid and by ultrasonic energy. Then the parent glass casting (after visual inspection for possible casting flaws) is mounted by button 34, and unsupported other than by the sprue and button, in a furnace. The temperature within the furnace is raised slowly at about 200° C./hour to about 1050°–1150° C., maintained thereat for about 4 hours, and thereafter cooled. Finally, sprue 34 and button 35 are removed by grinding and the surfaces of the cap are ground to finally adjusted shape.

It will be appreciated that, if desired, the parent glass casting can be heat treated while within the investment mold to effect crystallization thereof. This practice has the advantages of speeding production and fuel economy. Thus, rather than cooling the glass to room temperature and then reheating, the glass need only be cooled to below the transformation range thereof and thereafter reheated to the nucleation and crystallization temperature ranges. The investment material will then be removed mechanically from the crystallized casting. However, it is apparent that this practice does not permit inspection of the casting for flaws in the glass casting prior to crystallization. Moveover, at the elevated temperatures required in heat treating, the investment material is prone to sinter into a solid mass, rendering difficult removal from the casting.

As has been emphasized above, the three characteristics which materials designed for use in dental constructs must demonstrate are a particular visual appearance, as delineated in terms of translucency, excellent chemical durabilty within a pH range of about 6-8, and processibility, as measured in terms of thermal deformation or sag during the heat treatment cycle and the degree of contraction resulting from densification during conversion of the precursor glass body to a glass-ceramic.

Table I records a group of glass compositions, expressed in terms of parts by weight on the oxide basis, which illustrate the criticality of composition control to achieve the necessary balance of forming and physical properties to be suitable for the production of dental constructs and tools. It will be observed that the sum of the individual components totals somewhat over 100. This circumstance is the result of the oxygen correction required to compensate for stating the fluoride content separately. However, because this sum is not far removed from 100, for all practical purposes the individual values can be deemed to represent weight percent. The actual batch ingredients may comprise any materials, either oxides or other compounds, which, when melted together, are converted into the desired oxides in the proper proportions. The fluoride was incorporated into the batch as $MgF_2$, although it will be appreciated that other compounds can be utilized as a source thereof.

The batch ingredients were compounded, ballmilled together to secure a homogeneous mixture, deposited into platinum crucibles, lids placed upon the crucibles, and the crucibles introduced into a furnace operating at 1450° C. After a dwell period of four hours within the furnace, the melts were poured into glass slabs having the approximate dimensions of 8"×4"×0.5" (20×10×1.3 cm) and the slabs immediately transferred to an annealer set at a temperature of 500° C. The temperature of the annealer was raised to 620° C. and the slabs were annealed for about 0.5-0.75 hour. A visual description of the annealed glasses is reported in Table I.

preserve the beneficial effect of $Al_2O_3+ZrO_2$, but not to modify the forming and physical properties of the base glass, those additions were held constant.

In order to secure crystals of adequate size, i.e., >0.5 microns, in a highly crystalline body to insure the demanded high strength and translucency within a practical length of time, i.e., about 1-8 hours, the precursor glass will be exposed to temperatures between about 1050°-1150° C. and, preferably, in the vicinity of 1075°-1100° C. To eliminate any effect upon the physical characteristics of the exemplary compositions which modifications in heat treatment might exert, small pieces i.e., 3×3 cm, of each of the glasses in Table I were subjected to the following heat treatment in an electrically-fired furnace to develop tetrasilicic fluormica crystallization in situ:

Heat at 200° C./hour to 800° C.
No hold
Heat at 100° C./hour to 1075° C.
Hold for six hours
Cool furnace rate to room temperature (~3° C./minute)

Table II recites a qualitative assessment of the thermal deformation experienced by glass during this crystallization process along with a visual description of the outward appearance of each. Finally, an estimate of the grain size and extent of the crystallization, as obtained via a visual examination of fracture surfaces, is also recorded therein.

TABLE II

|  | 1 | 2 | 3 | 4 | 5 | 6 | 7 | 8 | 9 |
|---|---|---|---|---|---|---|---|---|---|
| Form | Held shape | Held shape | Completely deformed | Held shape | Completely deformed | Partially deformed | Held shape | Held shape | Highly deformed |
| Appearance | Very translucent | Opaque | — | Opaque | — | Very translucent | Very translucent | Very translucent | Very translucent |
| Surface Fracture | Smooth, silky | Fine-grained, smooth | Coarse, sugary | Fine-grained, smooth | Coarse, sugary, some glass | Smooth, silky | Smooth, silky | Smooth, silky | Smooth, silky, few spherulites |

Translucency is determined via reflectance measurements conducted by means of a laboratory exposure/photometer system utilizing both a white and a black background. The more highly translucent the material, the greater will be the spread between the white and black backed readings. Translucency T is defined as:

$$T = \frac{Y_W - Y_B}{Y_W - 4}$$

wherein $Y_W$ represents the luminous reflectance with a white background and $Y_B$ designated the luminous reflectance with a black background.

TABLE I

|  | 1 | 2 | 3 | 4 | 5 | 6 | 7 | 8 | 9 |
|---|---|---|---|---|---|---|---|---|---|
| $K_2O$ | 13.7 | 9.0 | 20.0 | 9.0 | 20.0 | 13.7 | 13.7 | 13.7 | 18.0 |
| MgO | 17.2 | 17.2 | 17.2 | 21.9 | 10.9 | 17.2 | 17.2 | 17.2 | 17.2 |
| $Al_2O_3$ | 0.5 | 0.5 | 0.5 | 0.5 | 0.5 | 0.5 | 0.5 | 0.5 | 0.5 |
| $SiO_2$ | 60.7 | 65.4 | 54.4 | 60.7 | 60.7 | 60.0 | 58.7 | 57.7 | 56.4 |
| $ZrO_2$ | 5.0 | 5.0 | 5.0 | 5.0 | 5.0 | 5.0 | 5.0 | 5.0 | 5.0 |
| F | 5.6 | 5.6 | 5.6 | 5.6 | 5.6 | 4.88 | 7.0 | 8.0 | 5.6 |
| Total | 102.7 | 102.7 | 102.7 | 102.7 | 102.7 | 101.28 | 102.1 | 102.1 | 102.7 |
| Visual Description | Clear | Clear, Slight surface crystal | Slight haze | Clear | Clear | Clear | Hazy patches | Cracked edges, center crystallized | Clear |

$Al_2O_3$ and $ZrO_2$ are advantageously included in the above exemplary compositions to improve the chemical durability and stain resistance thereof. Accordingly, to Table III reports levels of translucency measured on the glass-ceramic bodies of Table II. A preferred value of translucency has been deemed to range between about 0.50–0.70. Below 0.4 is definitely too opaque and above 0.8 too transparent.

An accelerated test for evaluating the chemical durability of the glass-ceramic bodies was developed wherein the amount of $K_2O$ extracted after exposure for four hours to water at 95° C. The test sample is a square having the dimensions of 5.1×2.5×0.3 cm which is polished on all sides. The square is immersed into 100 ml of water and the $K_2O$ extracted is expressed in terms of micrograms/cm$^2$ of surface area. To be considered acceptable, the level of $K_2O$ extracted will not exceed 10 micrograms/cm$^2$. Table III lists $K_2O$ values extracted for the glass-ceramics of Table II.

To evaluate the thermal deformation (sag) experienced by the glass-ceramic material during heat treatment, a bar having dimensions of 4.4×0.64×0.32 cm is cut from annealed glass and the surfaces subjected to a fine grind. The bar is centered across a 1.9 cm span with the 0.64 cm side down. The sag is measured in terms of mm as the movement of the bottom surface from its initial position. Values evidenced by several of the examples of Table II are recorded in Table III. A maximum sag of 8 mm is deemed acceptable.

The extent of densification undergone during the conversion of the parent glass to the glass-ceramic state is defined in terms of percent linear contraction and is calculated from density data. The density of the precursor glass and the density of the glass-ceramic, expressed in terms of grams/cm$^3$, and the calculated linear contractions are provided in Table III. To be tolerable, the linear contraction will not exceed 2%.

Finally, coefficients of thermal expansion, measured over the ranges of 25°–300° C. and 25°–500° C., exhibited by several of the glass-ceramics of Table II are recited in Table III in terms of ×10$^{-7}$/°C.

TABLE III

|  | 1 | 2 | 3 | 4 | 5 | 6 | 7 | 8 | 9 |
|---|---|---|---|---|---|---|---|---|---|
| Translucency | 0.630 | 0.139 | Melted | 0.010 | Melted | 0.647 | 0.603 | 0.525 | 0.677 |
| Durability | 1.2 | 0.6 | Devit | 2.4 | Melted | 0.6 | 3.5 | 4.7 | 15.0 |
| Sag | 4.4 | 0.33 | Devit | 0.127 | Melted | 5.3 | 2.36 | 1.14 | Melted |
| Glass Density | 2.565 | 2.572 | 2.590 | 2.613 | 2.514 | 2.571 | 2.641 | 2.707 | 2.584 |
| Glass-Ceramic Density | 2.679 | 2.686 | — | 1.806 | — | 2.667 | 2.728 | 2.847 | 2.682 |
| Linear Contraction | 1.4 | 1.4 | — | 2.3 | — | 1.2 | 1.1 | 0.5 | 1.2 |
| Coef. Exp. 25°–300° C. | 70.1 | 62.0 | — | 78.7 | — | 73.7 | 74.8 | 73.1 | 87.1 |
| Coef. Exp. 25°–500° C. | 74.3 | 66.4 | — | 82.4 | — | 76.3 | 77.0 | 76.6 | 89.8 |

The criticality of composition control, becomes immediately evident from an examination of Tables I–III. Thus, Examples 3 and 5 either melted and/or devitrified. Examples 2 and 4 are too opaque and Example 9 failed the durability and sag tests. Yet, those Examples were prepared from compositions closely approaching those of Examples 1 and 6–8. Example 1 is deemed to represent the most ideal combination of processing and physical properties.

Since certain changes may be made in the foregoing disclosure without departing from the objects hereof, it is intended that all matter described in the foregoing specification and shown in the accompanying drawings be interpreted in an illustrative and not in a limiting sense. Hence, as has been stated above, other forming techniques such as compression molding, centrifugal casting, and injection molding can be successfully employed.

I claim:

1. A glass-ceramic dental construct containing tetrasilicic fluormica as the predominant crystal phase and having surfaces that conform to and are in contact with living dental tissue, a modulus of rupture greater than 8000 psi and consisting, in weight percent on the oxide basis, of $K_2$: 10–18
MgO: 14–19
$SiO_2$: 55–65
$Al_2O_3$: 0–2
$ZrO_2$: 0–7
F: 4–9 said dential construct having a coefficient of thermal expansion and a thermal conductivity approximating those of tooth enamel, a visual appearance similar to that of tooth enamel, as evidenced by a level of translucency between 0.4–0.8 determined by reflectance measurements and resistance to food staining and chemical attack in an oral environment as evaluated by a level of $K_2O$ extracted not exceeding 10 micrograms/cm$^2$ after exposure for four hours to water at 95° C.

* * * * *